United States Patent
Machler et al.

(10) Patent No.: US 11,312,778 B2
(45) Date of Patent: Apr. 26, 2022

(54) METHOD FOR TREATING ALLERGIC CONTACT DERMATITIS

(71) Applicants: Brian C. Machler, Florham Park, NJ (US); Sharon E. Jacob, Loma Linda, CA (US)

(72) Inventors: Brian C. Machler, Florham Park, NJ (US); Sharon E. Jacob, Loma Linda, CA (US)

( * ) Notice: Subject to any disclaimer, the term of this patent is extended or adjusted under 35 U.S.C. 154(b) by 59 days.

Patent file contains an affidavit/declaration under 37 CFR 1.130(b).

(21) Appl. No.: 16/688,826

(22) Filed: Nov. 19, 2019

(65) Prior Publication Data

US 2020/0157229 A1 May 21, 2020

Related U.S. Application Data

(60) Provisional application No. 62/770,573, filed on Nov. 21, 2018.

(51) Int. Cl.
| | | |
|---|---|---|
| C07K 16/28 | (2006.01) | |
| A61K 39/395 | (2006.01) | |
| A61P 17/00 | (2006.01) | |
| A61P 37/08 | (2006.01) | |
| A61K 39/00 | (2006.01) | |

(52) U.S. Cl.
CPC ........ *C07K 16/2866* (2013.01); *A61K 39/395* (2013.01); *A61K 39/3955* (2013.01); *A61P 17/00* (2018.01); *A61P 37/08* (2018.01); *A61K 2039/505* (2013.01)

(58) Field of Classification Search
None
See application file for complete search history.

(56) References Cited

U.S. PATENT DOCUMENTS

| | | |
|---|---|---|
| 7,608,693 B2 | 10/2009 | Martin et al. |
| 8,980,273 B1 | 3/2015 | Clube |
| 8,986,691 B1 | 3/2015 | Clube |
| 2015/0246973 A1 | 9/2015 | Graham et al. |
| 2016/0193186 A1 | 7/2016 | Bozik et al. |
| 2018/0078603 A1 | 3/2018 | Radin et al. |
| 2018/0155436 A1 | 6/2018 | Orengo et al. |
| 2019/0183973 A1 | 6/2019 | Hamilton et al. |

FOREIGN PATENT DOCUMENTS

| | | |
|---|---|---|
| WO | 2012047954 | 4/2012 |
| WO | 2015130975 | 9/2015 |
| WO | 2018045130 | 3/2018 |
| WO | 2018057776 | 3/2018 |
| WO | 2018102597 | 6/2018 |

OTHER PUBLICATIONS

Wegmann et al, Expert Review of Respiratory Medicine, 2017; vol. 11, No. 9, pp. 675-677.*
Ul-Haq et al, Cytokine & Growth Factor Reviews, 2016, vol. 32, pp. 3-15.*
Borok et al, Clinical Reviews in Allergy & Immunology; 2019; vol. 56, pp. 86-98.*
Kostner et al, Immunology and Allergy Clinics of North America, Feb. 2017; vol. 37, No. 1, pp. 141-152.*
Yepes-Nunez et al, Allergol Immunopathol (Madr) 40(2): 126-128, 2012.*
Grey et al., Minnesota Medicine, Aug. 2016, pp. 48-49.*
Machler, Brian C., et al. "Dupilumab Use in Allergic Contact Dermatitis." Journal of the American Academy of Dermatology Aug. 28, 2018.
Machler, Brian C., et al. "Dupilumab Use in Allergic Contact dDrmatitis." Journal of the American Academy of Dermatology 80.1 (Jan. 2019): 280-281.
Jacob, Sharon E., et al. "Dupilumab for Systemic Allergy Syndrome With Dermatitis." Dermatitis 30.2 (Mar. 2019): 164-167.
Chipalkatti, Naina, et al. "A Retrospective Review of Dupilumab for Atopic Dermatitis Patients with Allergic Contact Dermatitis." Journal of the American Academy of Dermatology 80.4 (Apr. 2019): 1166-1167.
Yamane, Maya LM, et al. "Two Differing Presentations of Periocular Dermatitis as a Side Effect of Dupilumab for Atopic Dermatitis." Orbit (Jan. 10, 2019): 1-5.
Stout, Molly, et al. "Variable Impact of Dupilumab on Patch Testing Results and Allergic Contact Dermatitis in Adults With Atopic Dermatitis." Journal of the American Academy of Dermatology 81 (Mar. 15, 2019): 157-162.
Zhu, Gefei Alex, et al. "Repeat Patch Testing in a Patient with Allergic Contact Dermatitis Improved on Dupilumab." Journal of the American Academy of Dermatology case reports 5.4 (Apr. 2019): 336-338.
Crepy, Marie-Noëlle, et al. "Blocking Type 2 Inflammation by Dupilumab Does Not Control Classic (Type 1-Driven) Allergic Contact Dermatitis in Chronic Hand Eczema." Contact Dermatitis 81 (Mar. 9, 2019): 145-147.
Collantes-Rodríguez, Cristina, et al. "Recall Dermatitis at Patch Test Sites in an Atopic Dermatitis Patient Treated With Dupilumab." Contact Dermatitis 80.1 (2019): 69-70 (first published Oct. 17, 2018).
Suresh, Raagini, et al. "The Role of Expanded Series Patch Testing in Identifying Causality of Residual Facial Dermatitis Following Initiation of Dupilumab Therapy." Journal of the American Academy of Dermatology case reports 4.9 (Oct. 2018): 899-904.
Joshi, Shyam R., et al. "Effective Use of Dupilumab in Managing Systemic Allergic Contact Dermatitis." Dermatitis 29.5 (Sep. 2018): 282-284.
Chipalkatti N, et al. "Dupilumab as a Treatment for Allergic Contact Dermatitis" Dermatitis. 29(6) (Nov. 1, 2018): 347-8.
Goldminz AM, et al. "A Case Series of Dupilumab-Treated Allergic Contact Dermatitis Patients" Dermatologic Therapy. 31(6) (Nov. 2018):e12701 (first published Sep. 24, 2018).
Puza, Charles J., et al. "Positive Patch Test Reaction in a Patient Taking Dupilumab" Dermatitis 29.2 (Mar. 2018): 89.
Hoot, Joyce W., et al. "Patch Testing in a Patient on Dupilumab." Dermatitis 29.3 (May 2018): 164.
Hoot, J. W. "Dupilumab/Trolamine/Wool Fat." Reactions Jun. 16, 2018 p. 185.16 (1706).
Dupixent (dupilumab) injection Package Insert, Mar. 2017.

* cited by examiner

*Primary Examiner* — Bridget E Bunner
*Assistant Examiner* — Fozia M Hamud
(74) *Attorney, Agent, or Firm* — Florek & Endres PLLC; Martin Endres

(57) ABSTRACT

A method for treating allergic contact dermatitis comprising the administration of an interleukin-4 receptor alpha antagonist.

10 Claims, No Drawings

METHOD FOR TREATING ALLERGIC CONTACT DERMATITIS

This application claims the benefits of U.S. Provisional Patent Application No. 62/770,573 filed on Nov. 21, 2018, which is hereby incorporated by reference in its entirety.

FIELD OF THE INVENTION

The present invention relates to a method for treating allergic contact dermatitis (ACD) comprising administering a therapeutic amount of an interleukin-4 receptor (IL-4R) alpha antagonist, such as an IL-4R antibody to a patient with ACD.

BACKGROUND OF THE INVENTION

ACD is one of the most common skin conditions encountered within the dermatology clinic. ACD results from skin contact with a broad range of everyday encountered chemicals. Patient's with ACD may present clinically with treatment resistant rashes or skin lesion at the site of contact or exposure and the rashes and skin lesions may expand beyond the contact site and in some cases may involve the patient's entire body surface. Other symptoms of ACD may range from itching, skin redness, inflammation, and localized swelling to serious debilitating medical conditions with profound impact on the patient's quality of life and functionality.

Specifically, some patients with severe ACD often suffer from hand dermatitis, a manifestation of ACD that affects approximately 10% of the United States population, and often is associated with reduced quality of life and decreased career productivity. Hand dermatitis is triggered by irritants found in detergents, cosmetics, soaps, chemicals, and often affect cleaners, food caterers, hairdressers, healthcare workers, and mechanics who are in constant contact with these allergens and irritants on a daily basis. Thus, ACD patients with hand dermatitis (dermatitis involving the hand) are particularly challenging subset of ACD patients to treat given that patients have 1) difficulty avoiding the culprit allergen, 2) difficulty maintaining and reapplying topical corticosteroids on the hand, often due to career demands, and 3) the hand is the most frequent body part that individuals use to handle any objects in day to day living.

Some common allergens that may cause ACD include but are not limited to: bacitracin, benzalkonium (BAK), benzoyl peroxide, bronopol (2-bromo-2-nitro-1,3-propanediol), caine mix, carba mix (diphenylguanidine, zincdibutyldithiocarbamate, and zincdiethyldithiocarbamate), chromium, cobalt, cocamidopropyl betaine (CAPB), colophony (rosin), dihydrochloride, disperse blue mix, Euxyl K 400, formaldehyde, ethylenediamine, formaldehyde, fragrances (fragrance mix), gold, isothiazolinones, mercaptobenzothiazole, myroxylon *pereirae* (balsam of peru), neomycin, nickel, oleamidopropyl dimethylamine, palladium, quaternium-15, thiomersal, sandalwood, thiuram, and urushiol. In addition, some topical drugs such as antibiotics, anesthetics, antiseptics, and steroids as well as cosmetics may also cause ACD.

Treatments for ACD include allergen avoidance, administration of corticosteroids topically or systemically, as well as off-label use of potent systemic immunomodulatory agents such as cyclosporine (CysA), methotrexate, mycophenolate mofetil, etanercept, ustekinumab, apremilast, and azathioprine for moderate-to-severe-to-very severe cases where patients with ACD are not controlled by topical steroids alone. Patients often suffer from recurrent ACD flares requiring repeated dose of oral steroids or parenteral steroid administrations. There is currently no FDA indicated systemic treatment for ACD.

Absolute avoidance of common prevalent allergens, even after proper identification of culprit allergen, may not be possible or feasible and realistic for patients suffering from ACD. Unfortunately, ACD patients often resolve to being treated long term with systemic steroids and immunosuppressors at baseline or during flares. The severe side effects and limited therapeutic efficacy associated with broad systemic immunosuppressor agents including but not limited to broad immunosuppression, predisposition to infections, development of malignancies, gastritis, ulcerative stomatitis, gastric upset, myelosuppression, leukopenia, pulmonary fibrosis, transaminitis and hepatotoxicity, and diabetes, has created a demand for the utilization of both novel and currently existing novel precise immunological therapies that specifically target the pathophysiology behind the development of ACD.

The pathophysiology of ACD is perpetuated by a complex interplay between culprit sensitizing allergens and the patient's primary and secondary immune system. ACD is conventionally explained as a Type IV hypersensitivity sometimes referred to as delayed-type hypersensitivity (DTH) allergic reaction. DTH allergic reaction is induced after a patient comes in contact with a sensitizing allergen and is distinct from atopic diseases, such as atopic dermatitis, which are immediate hypersensitivity reactions (Type I hypersensitivity). DTH allergic reaction is a T-cell-driven process that involves the adaptive (secondary) immune system. In the traditional model for DTH allergic reaction, allergens presented by antigen-presenting cells promote the differentiation of progenitor T cells into primed helper T-cell subtypes through the release of specific immunomodulatory signals such as interferon γ (IFN-γ) and interleukins (ILs). Primed helper T-cell thereby activate cytotoxic CD8+ T cells to carry out cell-mediated adaptive immune responses and damage associated with ACD.

In essence, the TH1 (CD8+ T-cells, IFN-γ) pathway is associated with the perpetuation of ACD. It should be noted that ACD, a Type IV hypersensitivity reaction, is an immunological disease process distinct from atopic dermatitis/atopy, a Type I hypersensitivity reaction that involves the TH2 pathway (CD4+ T-cells, IL4, IL13). Thus, while ACD is known to perpetuate from the activity the TH1 immunological pathway, the role of the TH2 immunological pathway [interleukin 4 (IL-4) and interleukin 13 (IL-13)], the targets for dupilumab, has not been elucidated as a pathophysiological mechanism behind the manifestation of ACD.

SUMMARY OF THE INVENTION

The present invention relates to the treatment and/or prevention of ACD. More specifically the present invention relates to a method of use comprising the administration of interleukin-4 receptor (IL-4R) antagonists to patients with moderate-to-severe-to-very severe ACD who have failed systemic immunosuppressor treatments, have failed corticosteroid treatments (both topical and local) and have failed avoidance of the allergen.

The present invention comprises the step of administering a therapeutic amount of an interleukin-4 receptor antagonist, preferably an interleukin-4 receptor alpha antagonist to a patient with ACD. The ACD may be moderate, severe or very severe. A preferred interleukin-4 receptor alpha antagonist is dupilumab. In certain embodiments, the interleukin-4 receptor alpha antagonist is administered to provide systemic exposure to the interleukin-4 receptor alpha antagonist and may include intramuscular, intravenous, oral, parenteral, rectal, or vaginal delivery. A preferred method for administration is through subcutaneous injection, which may be administered by the patient or a health care provider such as a doctor, nurse or other health care aid.

Certain embodiments of the present invention include a method for treating and/or preventing ACD comprising improving at least one ACD-associated parameter such as Body Surface Area (BSA) involvement in a patient by administering a therapeutic amount of an interleukin-4 receptor antagonist, preferably an interleukin-4 receptor alpha antagonist to the patient and particularly a patient with moderate-or severe-or-very severe ACD.

Other embodiments of the present invention include a method for treating and/or preventing ACD comprising improving at least one ACD-associated parameter such as Body Surface Area (BSA) involvement in a patient wherein the patients exhibits a patch-test positive reaction to Fragrance Mix I, Fragrance Mix II, Balsam of Peru, ylang ylang, dithiodimethylene difuran, sandalwood/sandalwood oil, nickel, cobalt, palladium (Pd)/palladium chloride, gold sodium thiosulfate, methylisothiazoline and methylchloroisothiazolinone (MI/MCI), Amerchol L101, benzalkonium, Quaternium 15, thimerisol, formaldehyde, benzalkonium, Kathon CG, cocoamidoproprobetaine (CAPB), triethanolamine, oleamidopropyl dimethylamine, polysorbate 80/tween 80, propylene glycol, fungicide and/or antibiotics such as bioban, neomycin, Iodopropynyl butylcarbamate, bacitracin and thiomersal, Caine mix, carba mix, benzocaine, Hydrocortisone-17-butyrate, Clobetasol, thiuram, diphenylthiourea, 4-tert-butylcatechol, epoxyresin, shellac, disperse blue (dyes), octyl salicylate, lanolin or any combination of the foregoing. This method comprises administering a therapeutic amount of an interleukin-4 receptor antagonist, preferably an interleukin-4 receptor alpha antagonist to patients with ACD and particularly with moderate-or severe-or-very severe ACD.

One embodiment of the present invention comprises a method for treating and/or preventing ACD comprising administering a therapeutic amount of an interleukin-4 receptor antagonist, preferably an interleukin-4 receptor alpha antagonist to patients with moderate-or severe-or-very severe ACD who have failed to obtain adequate relief or reduction in ACD symptoms with other conventional ACD treatments such as administration of immunosuppressors, including but not limited to oral prednisone, cyclosporine, methotrexate, apremilast, azathioprine, mycophenolate mofetil, etanercept, and ustekinumab, and/or avoidance of contact inducing allergens.

Another embodiment of the present invention comprises a method for treating and/or preventing ACD comprising administering a therapeutic amount of an interleukin-4 receptor antagonist, preferably an interleukin-4 receptor alpha antagonist to patients with moderate-or severe-or-very severe ACD with a childhood history of atopic dermatitis.

A further embodiment of the present invention comprises a method for treating and/or preventing ACD comprising administering a therapeutic amount of an interleukin-4 receptor antagonist, preferably an interleukin-4 receptor alpha antagonist to patients with moderate-or severe-or-very severe ACD and with hand dermatitis.

DETAILED DESCRIPTION OF THE INVENTION

Before the present invention is further described, it is to be understood that this invention is not limited to the particular embodiments described. It is also to be understood that the terminology used herein is for the purpose of describing particular embodiments only and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The terms "treating" and "treat" may be used interchangeably and include ameliorating, mitigating, and reducing the instances of one or more ACD symptoms including but not limited to rashes or skin lesion at the site of contact or exposure, rashes and skin lesions at areas of the patient's body other than the site of contact or exposure, itching, skin redness, inflammation, localized swelling and combinations thereof.

The terms "preventing" and "prevent" may be used interchangeably and include stopping one or more ACD symptoms from presenting.

The term "moderate ACD" as used herein describes a moderate dermatitis disease process, visible involvement, moderate erythema, pruritus, moderate edema or infiltrate with scarce papules and no vesicles. The term "severe ACD" as used herein describes a severe dermatitis disease process with visible involvement, severe erythema, pruritus, severe/strong infiltration and itchiness, with numerous papules and/or vesicles. The term "very severe ACD" as used herein to describe a very severe dermatitis disease process with visible involvement, very severe erythema with significant infiltration with vesiculation/oozing, and/or presence of coalescing vesicles, bullae, or ulcerations, severe itchiness or presentation of pain. Body surface area (BSA) affected by the ACD is also considered, but not utilized solely as a definitive quantitative endpoint for determining severity.

The terms "administering" and "administer" are used interchangeably and include any mode of administration, such as oral, subcutaneous, sublingual, transmucosal, parenteral, intravenous, intra-arterial, buccal, sublingual, topical, vaginal, rectal, ophthalmic, otic, nasal, inhaled, and transdermal. "Administering" can also include prescribing or filling a prescription for a dosage form comprising the interleukin-4 receptor antagonist and at least one pharmaceutically acceptable excipient. "Administering" can also include providing directions to carry out the method of the invention involving the interleukin-4 receptor antagonist or a dosage form comprising the interleukin-4 receptor antagonist compound and at least one pharmaceutically acceptable excipient.

In certain embodiments of the present invention, the method for treating and/or preventing ACD comprises the parenteral administration, preferably subcutaneous administration, of about 100 to about 1,000 mg, preferably about 200 to about 800 mg and most preferably about 250 mg to about 750 mg of an interleukin-4 receptor antagonist, preferably an interleukin-4 receptor alpha antagonist and most preferably dupilumab. The parenteral administration of the interleukin-4 receptor antagonist, preferably the interleukin-4 receptor alpha antagonist and most preferably dupilumab may be administered as a single bolus or in 2-4 boluses injected into different sites such as the thigh, arm, abdomen or buttocks. If the administration occurs with 2-4 boluses, the second, third or fourth bolus should occur within 24 hours, preferably 12 hours, 11 hours, 10 hours, 9 hours, 8 hours, 7 hours, 6, hours, 5 hours, 4 hours, 3 hours, 2 hours, 1 hour, 0.5 hours or 0.25 hours of the first administration.

In certain embodiments, the method comprises an initial or first dose of dupilumab administered as previously described in 1-4 boluses and one or more subsequent doses or boluses administered about 5 days to about 21 days, preferably about 7 days to about 18 days and most preferably about 10 days to about 14 days after the initial dose or boluses and between subsequent doses or boluses. The subsequent dosing may be administered for as long as needed. In certain embodiments, the method comprises an initial administration and one or more subsequent administrations every 7 to 10 days after the initial administration for about 1 month, 2 months, 3 months, 4 months, 5 months, 6 months or longer.

In certain embodiments, dose of the subsequent administrations may be the same as the initial dose or may be about 25%, 30%, 35%, 40%, 45%, 50%, 55%, 60%, 65%, 70%, 75%, 80%, 85% or 90% of the initial dose. In a preferred embodiment of the present invention, the method for treating and or preventing ACD in a patient comprises subcutaneously administering an initial dose of about 500 mg to about 700 mg, preferably 600 mg of dupilumab to a patient with ACD and the administering subsequent doses of about 250 mg to about 350 mg, preferably about 300 mg of dupilumab every 10 to 18 days, preferably every 14 days after the initial dose as needed.

Patient's treated according to the methods described herein should exhibit at least a 40%, 45%, 50%, 55%, 60%, 70%, 75%, 80%, 85%, 90%, 95%, or 100% reduction in the Body Surface Area of skin affected by the ACD. Preferably the reduction in Body Surface Area of skin affected by the ACD should occur within 1 week, 2 weeks, 3 weeks, 4 weeks, 5 weeks, 6 weeks, 7 weeks, 8 weeks, 9 weeks, 10 weeks, 11 weeks or 12 weeks after the initial dosing.

In some embodiments of the present invention, the method for treating and/or preventing ACD by administering an interleukin-4 receptor antagonist, preferably an interleukin-4 receptor alpha antagonist and most preferably dupilumab further comprises the co-administration or concomitant administration of a corticosteroid, either topically or systemically.

The methods of the present invention are also useful to treat ACD that may be cause by allergens including but not limited to: Acrylates, Ammonium persulfatem, Avobenzone, Bacitracin, Balsam of Peru, Benzalkonium chloride, Benzocaine, Benzophenone, Bemotrizinol, Bisoctrizole, Bufexamac, Chrome, Cinnamate, Clioquinol, Cobalt, Coconut diethanolamide, Colophony, Compositae, Computer mouse, Cosmetics, Diethylthiourea Dimethyl fumarate, Ecamsule, Ensulizole, Epoxy resin, Ethylenediamine, Formaldehyde, Fragrances and perfumes, Glyceryl thioglycate (acid perming solution), Imidazolidinyl urea, Isopropynyl butylcarbamate, Isothiazolinone, Jewelry allergy, Kathon CG, Latex, Mercapto, Methyldibromo glutaronitrile, Methylisothiazolinone, Nail cosmetics, Neomycin, Nickel, PABA, Paraben mix, Paraphenylenediamine, Plants, P-tert butylphenol formaldehyde resin, Preservatives, Propolis, Quaternium-15, Rosin, Rubber accelerators, Salicylate, Sunscreens, Textile dyes, Thioglycolate, Thiomersal, Toothpaste, Topical medications such as antibiotics, anesthetics, antiseptics, and steroids, Wool alcohols (lanolin) and Foods and combinations thereof.

Some embodiments of the present invention comprise the subcutaneous administration of dupilumab as previously described to patients with ACD and particularly patients that failed to obtain satisfactory relief with other conventional treatments for ACD wherein the ACD was caused by patch-test proven contact with one or more of the following allergens:

Fragrances/food flavoring such as Fragrance Mix I, Fragrance Mix II, Balsam of Peru, ylang ylang, dithiodimethylene difuran, sandalwood/sandalwood oil and combinations thereof;

Metals such as nickel, cobalt, palladium (Pd)/palladium chloride, gold sodium thiosulfate and combinations thereof;

Preservatives such as methylisothiazoline and methylchloroisothiazolinone (MI/MCI), Amerchol L101, benzalkonium, Quaternium 15, thimerisol, formaldehyde, benzalkonium, Kathon CG and combinations thereof;

Surfactants/emulsifiers such as cocoamidoproprobetaine (CAPB), triethanolamine, oleamidopropyl dimethylamine, polysorbate 80/tween 80, propylene glycol and combinations thereof;

Bactericide, fungicide and/or antibiotics such as bioban, neomycin, Iodopropynyl butylcarbamate, bacitracin and thiomersal, and combinations thereof;

Anesthetics such as Caine mix, carba mix, benzocaine and combinations thereof;

Steroids such as Hydrocortisone-17-butyrate, Clobetasol and combinations thereof;

Rubber/rubber accelerators such as thiuram, diphenylthiourea and combinations thereof;

Resins such as 4-tert-butylcatechol, epoxyresin, shellac and combinations thereof;

Dyes such as disperse blue (dyes)

Sunscreens containing ingredients such as octyl salicylate

Waxes such as lanolin and any combination of the foregoing allergens.

Some embodiments of the present invention may also be used to treat ACD caused by contact with one or more of the following: bacitracin, balsam of Peru, chromium, cobalt, colophony (rosin), formaldehyde, fragrances, gold (gold sodium thiosulfate), isothiazolinones, mercaptobenzothiazole, neomycin, nickel, photographic developers, quaternium-15, tree and plant saps, platinum, thiomersal, topical drugs such as anesthetics, steroids, antibacterial, and antiseptics, urushiols and combinations thereof.

Example 1

A retrospective chart review was performed to identify patients treated with IL-4 receptor antagonists, dupilumab, (commercially available under the brand name DUPIXENT®) for recalcitrant dermatitis according the dosing and administration instructions provided with the 2017 FDA approved DUPIXENT® Prescribing Information which is incorporated herein by reference.

Patient Selection

The target population included adults with uncontrolled moderate-to-severe-to-very severe allergic contact dermatitis confirmed with patch testing who were not adequately controlled with broad spectrum systemic immunosuppressing therapies.

Inclusion criteria: A patient had to meet the following criteria for inclusion:
1) male or female;
2) age 18 or older;
3) a positive patch test to one or more contact allergen;
4) received dupilumab for at least 10 weeks;
5) a documented history of refractory allergic contact dermatitis inadequately treated with either inpatient or outpatient topical and systemic treatments [including both steroids and/or broad spectrum systemic immunomodulators, disease-modifying antirheumatic drugs (DMARDS)], and who were either unresponsive or experienced failure to maintain remission while undergoing course of treatment. Systemic immunosuppressors that patients failed to achieve adequate therapeutic response with includes but is not limited to oral prednisone, cyclosporine, methotrexate, apremilast, azathioprine, mycophenolate mofetil, etanercept, and ustekinumab. Inadequacy of treatment also determined by failure to maintain low disease state.
6) compliance with dupilumab treatment clinical visits and procedures.

Exclusion criteria: If a patient had one of the following criteria they were excluded from the study:
1) prior exposure to IL-4 receptor antagonists or dupilumab, treatment;
2) had not undergone prior treatment with a systemic immunomodulator/immunosuppressor;
3) exhibited successful control of ACD with topical or systemic therapies; and
4) known or suspected immunosuppression.

Procedures and Assessment

A retrospective chart review was performed to identify patients with patch-test proven allergic contact dermatitis who were treated with standard doses of dupilumab for recalcitrant dermatitis by a board-certified dermatologist. Clinical evaluations had been performed by a board-certified dermatologist as part of the clinical management, using a modified physician global assessment Modified Physician Global Assessment (mPGA) and body surface area (BSA) as quantitative clinical points of measurement, while extent of erythema/redness, vesicles, edema, and itchiness associated with skin and active allergic contact dermatitis lesions were qualitative clinical points of measurement considered. The modified Physician Global Assessment (mPGA) utilized alone is not standardized instruments for the classification of allergic contact dermatitis and each instrument has been modified and adapted to be applied to the clinical assessment and grading of allergic contact dermatitis. Albeit, there is currently no standardized grading system for grading the severity of ACD unanimously utilized by board-certified dermatologist providers treating ACD.

Modified PGA is utilized clinically to provide a meaningful qualitative assessment of the disease severity of each patient. Modified physician global assessment applied to ACD can be described as the following:
0=clear/absent of disease, no inflammatory sign of Allergic Contact Dermatitis;
1=minimal disease—near complete clearance but still involving perceptible erythema;
2=mild disease—mild nonpalpable erythema with mild infiltration, mild itchiness;
3=moderate disease—moderate palpable erythema with moderate infiltration and itchiness, scarce papules with no signs of vesicles, moderate itchiness;
4=severe disease—severe erythema with severe/strong infiltration and itchiness, with numerous papules and/or vesicles;
5=very severe disease—very severe erythema with severe infiltration with vesiculation/oozing, presence of coalescing vesicles, bullae, or ulcerations, severe itchiness or presentation of pain.

Patient's extent of ACD also includes calculating the percent Body Surface Area involved as a primary endpoint. Conventionally, the total body surface area calculation comprises of the summation of each body part. The head and neck, each arm, the front and back of each leg and the four trunk quadrants are assigned as 9% BSA, respectively, with 1% for the genitalia, for a total sum of 100% BSA. Subsequently, the proportion of involvement of each body part are further accessed during clinical examination for 1) whether the body part is affected by ACD, and 2) proportion of each body part affected by ACD, to calculate the total body surface area involved.

All patients had been assessed for body surface area (BSA) involvement, severity index, and itch at baseline and 10-12 weeks after starting dupilumab (DUPIXENT®). Patients received 600 mg subcutaneous injection at initiation of treatment (2-300 mg boluses) followed by 300 mg (single bolus) on a biweekly basis (approximately every 14 days after initial injection). After the 10-12 weeks, patients continued to receive clinical care on an as needed basis thereafter. Safety data during the patient's treatment course were monitored and reviewed on an ongoing basis. Patient's BSA percent involvement with allergic contact dermatitis was measured immediately prior to the initiation of dupilumab and once again at 10-12 weeks after dupilumab treatment. The safety of dupilumab therapy in this treatment population was assessed by obtaining detailed medical history, clinical evaluation of treatment emergent adverse events, detailed physical assessments and evaluations. Patients continued to receive clinical care on an as needed basis after the 10-12-week assessment accessed by the parameters of this study.

Statistical Analysis

Data points were analyzed using quantitative descriptive statistics, independent t-tests, correlations, paired-t test, and correlation-coefficients.

Results

Patient disposition and baseline characteristics: 15 adult patients suffering from severe-to-very-severe (mPGA: 4-5) ACD who have undergone dupilumab treatment were reviewed. All of the patients had used and failed both topical and oral medications for the treatment of allergic contact dermatitis including but not limited to oral prednisone, cyclosporine, methotrexate, apremilast, azathioprine, mycophenolate mofetil, etanercept, and ustekinumab. Many patients had patch test proven delayed type-IV hypersensitivities to allergens prior to onset of dupilumab treatment. In all, the 15 patients had documented patch-test proven sensitivities to 46 distinct allergens. The most frequent clinically relevant allergens were cocamido-propyl betaine (40%), nickel (33%), oleamidopropyl dimethylamine (27%), Myroxylon *pereirae* (20%) and fragrance mix 1 (20%).

Of the patient cohort, 73% the adult patients treated had a history of childhood atopic dermatitis and current hand dermatitis. Recalcitrant facial dermatitis was prevalent during the course of dupilumab (DUPIXENT®) treatment in a significant number of the cases. The present BSA affected by ACD ranged 10%-80% (mean 48%). The percent improvement in BSA achieved after dupilumab (DUPIXENT®) treatment ranged from 70%-100% BSA (mean −85% BSA).

The primary dependent variable to measure outcome was % body surface involvement (% BSA).

The % BSA between before and after 12-weeks of dupilumab treatment was extremely statistically significant [95% Confidence Interval (CI): 0.325984 to 0.505016; Standard error (SE)=0.044; P<0.0001]. No statistical significance was identified between % BSA improvement and the presence or absence of a history of childhood atopic dermatitis, (95% CI: −0.1597 to 0.0325); SE=0.044; P=0.1761). No statistical significance was identified between % BSA improvement and the presence or absence of hand dermatitis, (95% CI: −0.1452 to 0.0430); SE=0.044; P=0.2614). A weak-negative (R=−0.1181, R 2=0.0139) correlation between patient age and % BSA improvement. Gender, history of childhood atopic dermatitis, hand dermatitis involvement did not have a statistically significant relationship with % BSA improved in patients who have undergone dupilumab treatment.

Table 1 depicts demographic and clinical information, including areas involved, patch-test proven allergen sensitivities, previous failed systemic therapies, and treatment outcomes of 15 patients.

treated continuously as needed, all except one patient, elected to remain on dupilumab therapy given the extent of clinical improvement achieved.

The above data demonstrates that dupilumab and IL-4 inhibitor antagonists in general serve as a therapeutic target for treating severe ACD in patients. Moreover, the above data demonstrates that dupilumab and IL-4 inhibitor antagonists in general serve as a therapeutic target for treating severe ACD in patients with and without a past childhood history of atopic dermatitis. The results also demonstrate that dupilumab, and IL-4 inhibitor antagonists in general, are efficacious in treating ACD in both male and female patients with and without hand dermatitis involvement.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of

TABLE 1

Demographics of systematized patch test confirmed allergic contact dermatitis patients

| Patient no. | Patient age when dupilumab initiated | Sex | History of childhood atopic dermatitis | Hand involvement | BSA at onset of dupilumab, % | Estimated % improvement within 10-12 wk on dupilumab | Recalcitrant dermatitis sites while on dupilumab | Previously failed systemic therapies |
|---|---|---|---|---|---|---|---|---|
| 1 | 28 | F | Yes | Yes | 55 | 95 | Hands, feet | CysA, pred |
| 2 | 29 | M | Yes | Yes | 65 | 80 | Face | MM, CysA, methotrexate, pred |
| 3 | 35 | M | Yes | Yes | 50 | 80 | Face, arms, hands | CysA, apremilast, AZA, pred |
| 4 | 44 | F | Yes | Yes | 15 | 80 | Face | MM, pred |
| 5 | 53 | M | No | No | 65 | 100 | Legs | CysA, pred |
| 6 | 54 | F | Yes | Yes | 45 | 80 | Face | CysA, MM, methotrexate, pred |
| 7 | 54 | M | Yes | No | 30 | 90 | Face, scalp | CysA, MM, pred |
| 8 | 55 | F | Yes | Yes | 55 | 90 | Face, eyelids, chest, hands | MM, pred |
| 9 | 56 | F | Yes | Yes | 50 | 80 | Neck, face | CysA, pred |
| 10 | 58 | F | No | Yes | 50 | 95 | Face, eyelids, legs | CysA, ustekinumab, pred |
| 11 | 58 | F | No | Yes | 25 | 85 | Scalp, face, chest, arms, legs | CysA, ustekinumab, pred |
| 12 | 60 | M | Yes | Yes | 60 | 90 | Face, trunk, legs, hands | CysA, MM, pred |
| 13 | 64 | M | Yes | Yes | 80 | 70 | Arms, legs | CysA, MM, AZA, etanercept, pred |
| 14 | 69 | F | Yes | No | 65 | 85 | Face, eyelids, breast | CysA, MM, pred |
| 15 | 72 | F | No | No | 10 | 80 | Trunk | CysA, pred |

AZA, Azathioprine; BSA, body surface area; CysA, cyclosporine A; MM, mycophenolic acid; pred, rescue prednisone >3 times per year Based on the above data a 10-16 week, preferably a 10-14 week, and most preferably a 10-12-week course of dupilumab therapy can be used to successfully treat ACD. Patients with ACD may be treated beyond the time frame for 12 weeks designated by this study. All except one patient who was loss to follow up continued dupilumab treatment upwards of one year of duration, without modification of the standard dosage or frequency (600 mg initial followed by 300 mg every other week). Utilizing the modified Physician Global Assessment to quantify extent of allergic contact dermatitis involvement, all except one patient after remaining on dupilumab therapy for one year since the initiation of therapy achieved and maintained a score of 0-1 (complete clearance/absence of disease, minimal disease involvement with minimal erythema and clinical symptoms), accounting for quantitative percentage body involvement and qualitative disease severity (i.e. extent of itchiness, erythema/redness, vesicles). All of the patients remaining on dupilumab therapy sustained a dramatic reduction in frequency of visit to the dermatology clinic while regaining a substantial improvement in quality of life previously lost. Patients were limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

What is claimed is:

1. A method for treating allergic contact dermatitis (ACD) comprising parenterally administering a therapeutic amount of dupilumab to a patient in need of such treatment for at least 10 to 12 weeks wherein the ACD is caused by a reaction to cocamido-propyl betaine, nickel, oleamidopropyl dimethylamine, myroxylon *pereirae* or fragrance mix 1.

2. The method of claim 1 wherein the patient has failed to obtain adequate relief or reduction in ACD symptoms with the administration of oral prednisone, cyclosporine, methotrexate, apremilast, azathioprine, mycophenolate mofetil, etanercept, or ustekinumab.

3. The method of claim 1 wherein the ACD is caused by cocamido-propyl betaine.

4. The method of claim 1 wherein the ACD is caused by nickel.

5. The method of claim 1 wherein the ACD is caused by oleamidopropyl dimethylamine.

6. The method of claim 1 wherein the ACD is caused by myroxylon *pereirae*.

7. The method of claim 1 wherein the ACD is caused by fragrance mix 1.

8. The method of claim 1 wherein the patient has hand dermatitis.

9. The method of claim 1 wherein the patient has facial dermatitis.

10. A method for treating allergic contact dermatitis (ACD) comprising parenterally administering a therapeutic amount of dupilumab to a patient in need of such treatment for at least 10 to 12 weeks wherein the ACD is caused by a reaction to cocamido-propyl betaine, nickel, oleamidopropyl dimethylamine, myroxylon *pereirae* or fragrance mix 1 and wherein the patient has failed to obtain adequate relief or reduction in ACD symptoms with the administration of oral prednisone, cyclosporine, methotrexate, apremilast, azathioprine, mycophenolate mofetil, etanercept, or ustekinumab.

* * * * *